United States Patent [19]

Livingston, Jr. et al.

[11] Patent Number: 5,215,667
[45] Date of Patent: Jun. 1, 1993

[54] METHOD FOR SEPARATING WATER SOLUBLE NOBLE METAL CATALYST FROM A NOBLE METAL CATALYZED HYDROFORMYLATION REACTION

[75] Inventors: Joel R. Livingston, Jr., Basking Ridge; Edmund J. Mozeleski, Califon; Guido Sartori, Annandale, all of N.J.

[73] Assignee: Exxon Chemical Patents Inc., Linden, N.J.

[21] Appl. No.: 747,597

[22] Filed: Aug. 20, 1991

[51] Int. Cl.$^5$ .............................................. B01D 61/14
[52] U.S. Cl. ................................. 210/651; 210/500.36
[58] Field of Search ............... 210/649, 650, 651, 652, 210/653, 654, 655, 500.36, 500.42

[56] References Cited

U.S. PATENT DOCUMENTS

| | | | |
|---|---|---|---|
| 3,617,553 | 11/1971 | Westaway et al. | 210/651 |
| 3,956,112 | 5/1976 | Lee et al. | 210/22 C |
| 3,966,595 | 6/1976 | Gosser | 210/651 X |
| 4,306,085 | 12/1981 | Kim et al. | 210/638 |
| 4,430,222 | 2/1984 | Walker | 210/477 |
| 4,525,276 | 6/1985 | Toda et al. | 210/433.2 |
| 4,625,067 | 11/1986 | Hanin | 568/451 |
| 4,625,068 | 11/1986 | Young | 568/454 |
| 4,642,388 | 2/1987 | Young | 568/454 |
| 4,689,152 | 8/1987 | Liang | 210/649 |
| 4,716,250 | 7/1986 | abatjoglou et al. | 568/454 |
| 4,731,486 | 11/1986 | Abatjoglou et al. | 568/451 |
| 4,732,671 | 3/1988 | Thornton et al. | 210/86 |
| 4,754,089 | 6/1988 | Matson et al. | 570/260 |
| 4,861,918 | 8/1988 | Miller et al. | 568/454 |
| 4,921,612 | 5/1990 | Sirkar | 210/644 |

FOREIGN PATENT DOCUMENTS

| | | |
|---|---|---|
| 740956 | 3/1970 | Belgium . |
| 752124 | 12/1970 | Belgium . |
| 890210 | 3/1982 | Belgium . |
| 2000196 | 6/1988 | Canada . |
| 88955 | 9/1983 | European Pat. Off. . |
| 133410 | 2/1985 | European Pat. Off. . |
| 157316 | 10/1985 | European Pat. Off. . |
| 163233 | 12/1985 | European Pat. Off. . |
| 163234 | 12/1985 | European Pat. Off. . |
| 173219 | 3/1986 | European Pat. Off. . |
| 216314 | 4/1987 | European Pat. Off. . |
| 216315 | 4/1987 | European Pat. Off. . |
| 269011 | 6/1988 | European Pat. Off. . |
| 269964 | 6/1988 | European Pat. Off. . |
| 167736 | 8/1988 | European Pat. Off. . |
| 354588 | 8/1988 | European Pat. Off. . |
| 355837 | 8/1988 | European Pat. Off. . |
| 302375 | 2/1989 | European Pat. Off. . |
| 0374615 | 12/1989 | European Pat. Off. . |
| 352478 | 1/1990 | European Pat. Off. . |
| 1953641 | 1/1971 | Fed. Rep. of Germany . |
| 2627354 | 12/1976 | Fed. Rep. of Germany . |

OTHER PUBLICATIONS

J. Israeli, et al., "Separator for immiscible Liquids", Ger. Offen., 2,342,324, Mar. 21, 1974, p. 18.
Edward Wolynic et al., "The catalytic liquid membrane reactor", Chemtech, Feb. 1974, pp. 111–117.

(List continued on next page.)

Primary Examiner—Frank Spear

[57] ABSTRACT

A method for separating a water soluble Group VIII noble metal catalyst from the crude reaction product of a noble metal-catalyzed hydroformylation reaction run in aqueous solution, in an aqueous emulsion or as an aqueous suspension, the crude reaction product including an aqueous phase containing a water soluble Group VIII noble metal-ligand complex catalyst, and an organic phase containing unreacted olefin feed and an organic hydroformylation reaction product, which comprises: (a) contacting the crude reaction product with a hydrophobic membrane capable of allowing a substantial portion of the unreacted olefin feed and the organic hydroformylation reaction product to pass therethrough while retaining a substantial portion of the water soluble Group VIII noble metal-ligand complex catalyst; (b) removing unreacted olefin feed and organic hydroformylation reaction product which passes through the hydrophobic membrane as permeate; and (c) retaining the water soluble Group VIII noble metal-ligand complex catalyst as retentate.

20 Claims, 3 Drawing Sheets

FOREIGN PATENT DOCUMENTS

| | | |
|---|---|---|
| 2946067 | 5/1981 | Fed. Rep. of Germany . |
| 3235029 | 3/1984 | Fed. Rep. of Germany . |
| 3245318 | 8/1984 | Fed. Rep. of Germany . |
| 3530839 | 8/1985 | Fed. Rep. of Germany . |
| 3443474 | 5/1986 | Fed. Rep. of Germany . |
| 3546123 | 6/1987 | Fed. Rep. of Germany . |
| 3616057 | 11/1987 | Fed. Rep. of Germany . |
| 3630587 | 3/1988 | Fed. Rep. of Germany . |
| 3842819 | 12/1988 | Fed. Rep. of Germany . |
| 2478078 | 9/1981 | France . |
| 55-92339 | 7/1980 | Japan . |
| 58-216138 | 12/1983 | Japan . |
| 59-004402 | 1/1984 | Japan . |
| 60-061005 | 4/1985 | Japan . |
| 61-238751 | 10/1986 | Japan . |
| 62-030734 | 2/1987 | Japan . |
| 63-044904 | 2/1988 | Japan . |
| 8700881 | 4/1987 | Netherlands . |
| 938516 | 11/1984 | U.S.S.R. . |
| 1266180 | 11/1971 | United Kingdom . |
| 1260733 | 1/1972 | United Kingdom . |
| 1312076 | 3/1973 | United Kingdom . |
| 1432561 | 11/1974 | United Kingdom . |
| 1594603 | 8/1981 | United Kingdom . |
| 8804286 | 12/1986 | World Int. Prop. O. . |

OTHER PUBLICATIONS

Gosser et al., "Reverse Osmosis in Homogeneous Catalysis", Journal of Mol. Catalysis, 2(1977), pp. 253–263.
Keurentjes et al., "Surfactant-Induced Wetting ...", Colloids Surf. vol. 51, 1990, pp. 189–206.
G. K. Anderson, "Oil Water separation with surface modified Membranes", Environ. Technol. Lett., vol. 8, No. 3, 1987, pp. 121–132.
Qiulin Wu, "The mechanism of membrane phase separation", Desalination, vo. 62, pp. 69–78 (1987).
Bapat et al., "Phase separation technique for liquid dispersion", Ind. Eng. Chem. Fundam., 23(1), pp. 120–123 (1984).
"Membranes: the new actors in liquid separations", Chemical Eng. vol. 96, No. 12, Dec. 1989, pp. 37–41.
Jáe Seung Kim, "Porous-walled and membrane reactor-sparators for heter. and hom. catalysis", Univ. Microfilms Int. Order No. DA8721416. (1988).
Ming Chao Kuo, "Heter. homo Catalyst", Ind. Eng. Chem. Res., 26(6), pp. 1140–1147 (1987).
Wandrey et al., "Continuous Cofactor regeneration in membrane reactors", Eur. Congr. Biotech., 3rd, vol. 1, pp. 239–244 (1984).
Bueckmann et al. "An efficient synthesis ...", J. Appl. Biochem., 3(4), pp. 301–315 (1981).
Wandrey et al., "Immobilization of biocatalysts using UF techniques", Eur. Cong. Biotech., 1st, pp. 44–47 (1978).
Schurig et al., "A new class of catalysts", Chemtech, 6(3), 212–14, (1976).
Cütler, et al. "Studies on a homo. coper catalyst ...", Intersoc. Energy Convers. Eng. conf., 8th, 86–90 (1973).

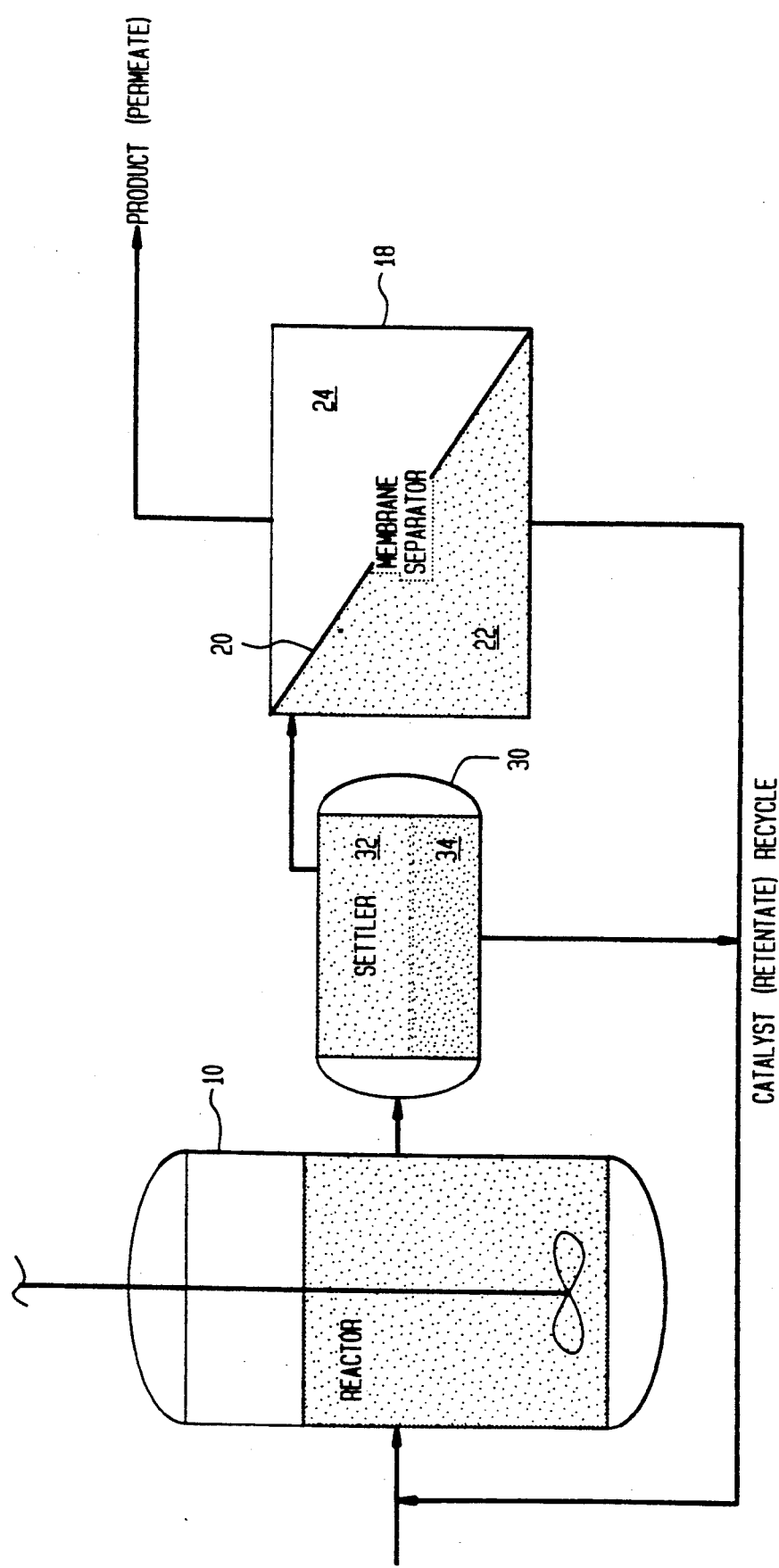

METHOD FOR SEPARATING WATER SOLUBLE NOBLE METAL CATALYST FROM A NOBLE METAL CATALYZED HYDROFORMYLATION REACTION

This invention relates to a method for separating water soluble Group VIII noble metal-ligand complex catalysts from the crude reaction product of a noble metal-catalyzed hydroformylation reaction by contacting the crude reaction product to a hydrophobic membrane whereby the water soluble Group VIII noble metal-ligand complex catalysts are retained by the membrane as retentate, and the unreacted olefin feed and the hydroformylation reaction product are passed through the membrane as permeate.

BACKGROUND OF THE INVENTION

Hydroformylation reactions involve the preparation of oxygenated organic compounds by the reaction of carbon monoxide and hydrogen (synthesis gas) with carbon compounds containing olefinic unsaturation. The reaction is typically performed in the presence of a carbonylation catalyst and results in the formation of compounds, for example, aldehydes, which have one or more carbon atoms in their molecular structure than the starting olefinic feedstock. By way of example, higher alcohols may be produced in the so-called oxo process by hydroformylation of commercial $C_6$–$C_{12}$ olefin fractions to an aldehyde-containing oxonation product, which on hydrogenation yields the corresponding $C_7$–$C_{13}$ saturated alcohols. The oxo process is the commercial application of the hydroformylation reaction for making higher aldehydes and alcohols from olefins. The crude product of the hydroformylation reaction will contain catalyst, aldehydes, alcohols, unreacted olefin feed, synthesis gas and by-products.

A variety of transition metals catalyze the hydroformylation reaction, but only cobalt and rhodium carbonyl complexes are used in commercial oxo plants. The reaction is highly exothermic; the heat release is ca 125 kJ/mol (30 kcal/mol). The position of the formyl group in the aldehyde product depends upon the olefin type, the catalyst, the solvent, and the reaction conditions. Reaction conditions have some effect and, with an unmodified cobalt catalyst, the yield of straight chain product from a linear olefin is favored by higher CO partial pressure. In the hydroformylation of terminal olefinic hydrocarbons, the use of a catalyst containing selected complexing ligands, e.g., tertiary phosphines, results in the predominant formation of the normal isomer.

In commercial operation, the aldehyde product usually used as an intermediate which is converted by hydrogenation to an alcohol or by aldolization and hydrogenation to a higher alcohol. The aldol-hydrogenation route is used primarily for the manufacture of 2-ethylhexanol from propylene via n-butyraldehyde.

The hydroformylation reaction is catalyzed homogeneously by carbonyls of Group VIII metals but there are significant differences in their relative activities. Roelen, using a cobalt catalyst, discovered hydroformylation in 1938. Dicobalt octacarbonyl, $Co_2(CO)_8$, which either is introduced directly or formed in situ, is the primary conventional oxo catalyst precursor. Using an unmodified cobalt catalyst, the ratio of linear to branched aldehyde is relatively low.

Much oxo research in the past 25 years has been directed to improving reaction selectivity to the linear product. Introduction of an organophosphine ligand to form a complex, e.g., $Co_2(CO)_6[P(n-C_4H_9)_3]_2$, significantly improves the selectivity to the straight-chain alcohol.

Recent developments of low pressure rhodium catalyst systems have been the subject of a considerable body of patent art and literature, and rhodium-triphenyl phosphine systems have been widely, and successfully, used commercially for the hydroformylation of propylene feedstocks to produce butyraldehyde.

The first commercial oxo process to employ a rhodium-modified catalyst was developed by Union Carbide, Davy Powergas, and Johnson Matthey. In this application, the complexed rhodium catalyst is dissolved in excess ligand and the reaction is run at relatively low pressures and temperatures as compared to a conventional oxo process. The ratio of normal to iso isomers is high relative to conventional oxo processes and so is favored as a process for the production of N-butyraldehyde.

A recent process commercialization has been that of Rhone-Poulenc and Ruhrchemie which produces butyraldehyde from propylene but the ligand is a sulfonated triphenylphosphine and is utilized as a water soluble sodium salt. Turnover rates are less than in the all-organic system, but the normal to iso ratios are high and the catalyst may be separated easily from the reaction product by separation of the aqueous layer containing the catalyst and the organic layer which constitutes the product.

In the formation of linear aldehydes using a ligand-modified rhodium-catalyzed homogenous process, the reactor comprises the rhodium complex catalyst, excess triphenylphosphine and a mixture of product aldehydes and condensation by-products. The product aldehyde may be recovered from the mixture by volatilization directly from the reactor or by distillation in a subsequent step. The catalyst either remains in or is recycled to the reactor. However, the complex catalyst and triphenylphosphine ligand are slowly deactivated and eventually the spent catalyst is removed for recovery of rhodium and reconversion to the active catalyst. This process, although effective for lower molecular weight aldehyde production, is not favored for higher molecular weight aldehydes which are higher boiling, distillation temperatures needed for aldehyde recovery are higher and catalyst deactivation is accelerated.

The aqueous ligand system is also very effective for propylene but higher molecular weight olefin feeds are not sufficiently soluble in the aqueous catalyst medium to allow acceptable rates of aldehyde formation. Thus, although separation of the higher molecular weight aldehyde should be more facile than the all-organic system, the slow rates preclude commercial acceptability.

In some cases, such as where the products of the reaction are relatively high boiling or where the olefin feed is not sufficiently soluble in water to permit satisfactory reaction rates, neither the process where the products are removed from the catalyst by distillation or stripping nor where the products are decanted from an aqueous catalyst solution may be utilized successfully. In such cases, it may be advantageous to utilize an aqueous medium to contain the catalyst and add a surfactant to enhance phase contacting so as to improve rate and selectivity to the desired products. This type of process is called "Phase Transfer Catalysis." However, when the surfactant is added, some carry-over of the noble metal into the organic phase at the conclusion of the process often results.

The present inventors have discovered that when they satisfactorily hydroformylated olefins in the presence of water soluble Group VIII noble metal-ligand complex catalysts using an aqueous-organic medium enhanced by surfactants, the catalyst can be recovered quantitatively from a crude reaction product which includes both an aqueous phase and an organic phase by employing membrane separation either internal or external to the hydroformylation reactor.

It has been known to use membranes to separate catalysts from an aqueous solution. An example is set forth in European Patent No. 0 263 953, published on Aug. 29, 1986 (assigned to Ruhrchemie Aktiengesellschaft), which discloses a process for separating rhodium complex compounds, which contain water-soluble organic phosphines as ligands, from aqueous solutions in which excess phosphine ligand and, if necessary, other components are also dissolved, is characterized by the fact that the aqueous solution is subjected to a membrane separation process. According to this process, volatile organic substances are separated from the solution prior to conducting the membrane separation process. A typical membrane for use in this process is a cellulose acetate membrane. This process only involves the separation of water-soluble ligands and noble metal catalyst from an aqueous solution. As such, this separation process does not pertain to the separation of a water soluble noble metal catalyst and a water soluble ligand from an organic-aqueous emulsion, dispersion or suspension produced from the hydroformylation process.

Another patent which utilizes cellulose acetate, silicone rubber, polyolefin or polyamide membranes in the separation of catalysts from high boiling by-products of the hydroformylation reaction is Great Britain Patent No. 1312076, granted on May 15, 1970. According to this patent the aldehydes produced during the hydroformylation process are continuously withdrawn as an overhead vapor stream. The liquid stream containing the heavy by-products with the catalyst is passed over a membrane wherein approximately 78-94.3% of the catalyst is retained and the heavy by-products permeated. This is an unacceptably low level of catalyst retention which is overcome by the process of the present invention.

In like manner, Great Britain Patent No. 1432561, granted on Mar. 27, 1972, (assigned to Imperial Chemical Industries LTD.) discloses a process for the hydroformylation of olefins which comprises reacting an olefin at elevated temperature and pressure with CO and $H_2$ in the presence of a compound of a group VIII metal and a biphyllic ligand of a trivalent P, As or Sb to give a crude liquid hydroformylation product containing an aldehyde and/or an alcohol, separating the aldehyde and/or alcohol from the crude product and leaving a liquid, bringing the liquid after separation of the Group VIII metal compound and free from aldehyde and alcohol under reverse osmosis conditions into contact with one side of a silicone rubber semi-permeable membrane in which the polymer chains have been at least partly cross-linked by gamma radiation whereby the liquid retained by the membrane contains a higher concentration of Group VIII metal compounds and/or biphyllic ligand than the original liquid.

In the article by Gosser et al., entitled "Reverse Osmosis in Homogeneous Catalysis," *Journal of Molecular Catalysis*, Vol. 2 (1977), pp. 253-263, a selectively permeable polyimide membrane was used to separate soluble transition metal complexes from reaction mixtures by reverse osmosis. For example, separation of cobalt and rhodium complexes from hydroformylation products of 1-pentene. That is, a solution of 0.50 g of $RhH(CO)(PPh_3)_3$ in 40 ml of benzene and 10 ml of 1-pentene was stirred at 50° C. with a $CO/H_2$ mixture at ca. 4 atm pressure until no further pressure drop occurred. The pentene was completely converted to aldehydes according to proton nmr analysis. The solution was permeated through a polyimide membrane under 68 atm nitrogen pressure. The permeate (4.5 g passed in 2 min.) showed only 9% of the original rhodium concentration by X-ray fluorescence.

The permeation rate of rhodium as set forth above, i.e., 9%, is considered unacceptable. The rhodium catalyst should be retained in an amount of greater than 99.5% to be a commercially feasible process.

Another example of the use of membranes to separate metal catalysts from hydroformylation products is set forth in Dutch Patent No. 8700881, published on Nov. 1, 1988. The method disclosed therein relates to one which improves the efficiency of membrane separation of hydroformylation products from expensive organometallic catalyst containing reaction mixtures. In Dutch Patent No. 87/881 a polydimethylsiloxane membrane having a thickness of 7 microns applied to a Teflon ® support was used in the separation of a reaction mixture containing $C_9$–$C_{15}$ alcohols, a homogeneous catalyst system comprising an organometallic complex of a transition metal from Group VIII or VIIa or Va of the Periodic Table, e.g., a tricarbonyl(triphenylphosphine) cobalt catalyst, and 40% low-viscosity lubricating oil (an antiswelling or de-swelling agent). At a flow of 133 $kg/m^2$-day, the cobalt contents in the feed, retentate, and permeate were 600, 910, and 18 ppm, verses 840, 1930, and 160 ppm, respectively, for a mixture without the de-swelling agent. This process is directed to the separation of product from a reaction mixture containing a homogeneous catalyst system by means of a membrane, whereas the present invention is directed to a heterogeneous catalyst system comprising both an organic and an aqueous layer. The ligands disclosed in Dutch Patent No. 8700881 are all organic soluble ligands, e.g., triphenylphosphine, tri-n-alkylphosphine or acetyl acetonate, whereas those used in the present invention are water soluble ligands. Critical to the process of Dutch Patent No. 8700881 is the addition of a de-swelling agent to the reaction mixture which assists in the separation of the products from the reaction mixture.

Each of the aforementioned processes for removing metal catalysts from crude hydroformylation reaction products are both costly in terms of unrecovered catalyst and, as such, would require further expensive treatment of the streams to recover catalyst.

The present invention provides a ligand and membrane combination which allows for the retention of over 99.5% of the noble metal catalyst from the hydroformylation reaction product which is passed over the membrane. Moreover, the hydrophobic membrane used in accordance with the process of the present invention remains thermally and hydrolytically stable during separation.

The present inventors have been able to demonstrate that an aqueous-organic-catalyst mixture can be separated from the crude hydroformylation product mixture using a hydrophobic membrane and a perstracting organic solvent. This novel process permits the organic products to permeate through the membrane, while retaining the rhodium catalyst and all other water soluble components.

The present invention also provides many additional advantages which shall become apparent as described below.

SUMMARY OF THE INVENTION

The present invention relates primarily to a process wherein an aqueous emulsion, suspension or dispersion of a crude reaction product comprising a water soluble Group VIII noble metal-ligand complex catalyst, unreacted olefin feed and a hydroformylation reaction product is contacted with or passed over a hydrophobic membrane capable of retaining the water soluble rhodium-ligand complex catalyst as retentate and permitting the unreacted olefin feed and organic hydroformylation reaction product comprising higher aldehydes and higher alcohols to permeate therethrough. Optionally, the aqueous emulsion, suspension or dispersion is first settled before delivering the organic phase, i.e., the hydroformylation reaction product with smaller amounts of the water soluble Group VIII noble metal-ligand complex catalyst, to the membrane for separation. It is also optional to add a surfactant to the noble metal-catalyzed hydroformylation reaction. Typical olefins used in the aforementioned hydroformylation process are $C_4$ to $C_{20}$, preferably $C_6$ to $C_{16}$.

The following is a preferred method for separating a water soluble noble metal catalyst from the crude reaction product of a noble metal-catalyzed hydroformylation reaction run in aqueous solution, in an aqueous emulsion or as an aqueous suspension. The crude reaction product includes an aqueous phase containing a water soluble Group VIII noble metal-ligand complex catalyst, and an organic phase containing unreacted olefin feed and an organic hydroformylation reaction product. The method comprises the following steps: (a) contacting the crude reaction product with a hydrophobic membrane capable of allowing a substantial portion of the unreacted olefin feed and the organic hydroformylation reaction product to pass therethrough while retaining a substantial portion of the water soluble Group VIII noble metal-ligand complex catalyst; (b) removing unreacted olefin feed and organic hydroformylation reaction product which pass through the hydrophobic membrane as permeate; and (c) retaining the water soluble Group VIII noble metal-ligand complex catalyst as retentate in an amount of about 99.5% or greater.

The noble metal-catalyzed hydroformylation reaction preferably includes the steps of: reacting an olefin with hydrogen and carbon monoxide in the presence of a water soluble Group VIII noble metal-ligand complex catalyst, at a temperature in the range between about 80° to 125° C. to produce an aldehyde having a normal aldehyde to isomeric aldehyde ratio in the range of between about 0.5:1 to about 80:1.

The ligand is preferably at least one compound selected from the group consisting of: Na-p-(diphenylphosphine)benzoate, Na-m-(diphenylphosphino)benzenesulfonate, and tri-(sodium m-sulfophenyl)-phosphine.

The surfactant is preferably at least one compound selected from the group consisting of cetyltrimethylammonium bromide, sodium laurate, sodium stearate, and linear dodecylbenzene sulfonate.

The hydrophobic membrane is preferably one membrane selected from the group consisting of: a high density polyethylene crosslinked membrane, a natural latex rubber membrane, a polyvinylidene difluoride membrane, a polychlorotrifluoroethylene membrane, and a polytetrafluoroethylene membrane.

A further object of the present invention is a method for producing higher aldehydes and higher alcohols which comprises: (a) hydroformylating an olefinic feedstock with synthesis gas in the presence of a water soluble Group VIII noble metal-ligand complex catalyst to form a crude reaction product comprised of an organic phase containing higher aldehydes, higher alcohols and secondary products and an aqueous phase containing a water soluble Group VIII noble metal-ligand complex catalyst; (b) removing the water soluble noble metal catalyst from the crude reaction product by feeding the crude reaction product to a membrane separator which comprises a hydrophobic membrane capable of allowing a substantial portion of the hydroformylation product, i.e., higher aldehydes, higher alcohols and secondary products, and unreacted olefin feed to pass therethrough while retaining a substantial portion of the water soluble Group VIII noble metal-ligand complex catalyst; (c) recovering the higher aldehydes, higher alcohols and secondary products as permeate; (d) retaining the water soluble Group VIII noble metal-ligand complex catalyst as retentate; and (e) recycling the retained water soluble Group VIII noble metal-ligand complex catalyst to the hydroformylation step (a).

Optionally, the aforementioned method includes the additional step wherein the crude reaction product is separated into an aqueous layer and an organic layer before it is fed to the membrane separator. The organic layer thereafter being fed to the membrane separator and the aqueous layer and retentate from the membrane separator are recycled to the hydroformylation reactor.

The noble metal-catalyzed hydroformylation reaction typically involves the reacting of a linear alpha olefin with carbon monoxide, and hydrogen in the presence of a water soluble Group VIII noble metal-ligand complex catalyst, at a temperature in the range between about 80° to 125° C. and a pressure of 1 to 100 atmospheres to produce an aldehyde having a normal to iso ratio in the range of between about 0.5:1 to about 80:1.

Other and further objects, advantages and features of the present invention will be understood by reference to the following specification in conjunction with the annexed drawings, wherein like parts have been given like numbers.

BRIEF DESCRIPTION OF THE DRAWINGS

FIG. 3 is schematic representation of another embodiment of the membrane reactor system according to the present invention which includes a settling tank used to settle the aqueous and organic phases of the crude reaction product before delivering the organic phase to the membrane separator.

DESCRIPTION OF THE PREFERRED EMBODIMENTS

Hydroformylation is a process of converting olefins to a product of one or more additional carbon numbers by the addition of carbon monoxide and hydrogen to the double bond(s) of the olefin in the presence of a catalyst at elevated temperatures and pressures. A typical hydroformylation process is demonstrated below:

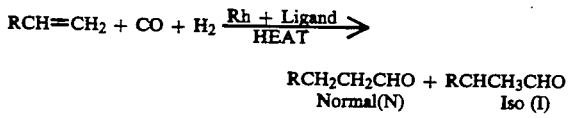

At a temperature of 100° C. and a pressure of 150 lbs. the normal to iso ratio using rhodium as the catalyst may be below 1 or even as high as 100, depending on the ligand, ratio of ligand to rhodium, etc. When cobalt is used as the catalyst and is not modified by a ligand, the normal to iso ratio is below 3 at most.

Another method for catalytic hydroformylation of olefins, using a conventional approach is set forth in U.S. Pat. No. 4,399,312 (Russell et al.), which issued on Aug. 16, 1983. The hydroformylation method discussed in the above-mentioned patent involves the reacting together, at elevated temperature and pressure, of an olefin, $H_2$ and CO in the presence of a catalyst comprising a water soluble complex of a noble metal and an amphiphilic reactant in a reaction medium comprising an aqueous phase and an organic phase. The organic phase includes a highly reactive olefin, e.g., $C_3-C_{20}$, and a solvent. The noble metal catalyst is typically Pt, Rh, Ru or Pd. The aqueous phase preferably contains a water-soluble phosphine in complex combination with a complex or catalytic precursor of the noble metal, e.g., sulfonated or carboxylated triaryl phosphines. The amphiphilic reagent is typically an anionic, nonionic or cationic surfactant or phase transfer agent such as a complex ammonium salt or a polyoxyethylene nonionic surfactant. The preferred ratio of aqueous phase to organic phase is 0.33:1 to 5:1, the ratio of $H_2$ to CO is 1:1 to 5:1, the content of precious metal in the aqueous phase is 100–500 ppm and the ratio of amphiphilic reagent to precious metal is up to 100:1 on a molar basis. It is preferable that the reaction be carried out at 300–10,000 kPa, especially 300–3,000 kPa and at a temperature in the range between about 40°–150° C.

Figure 1:
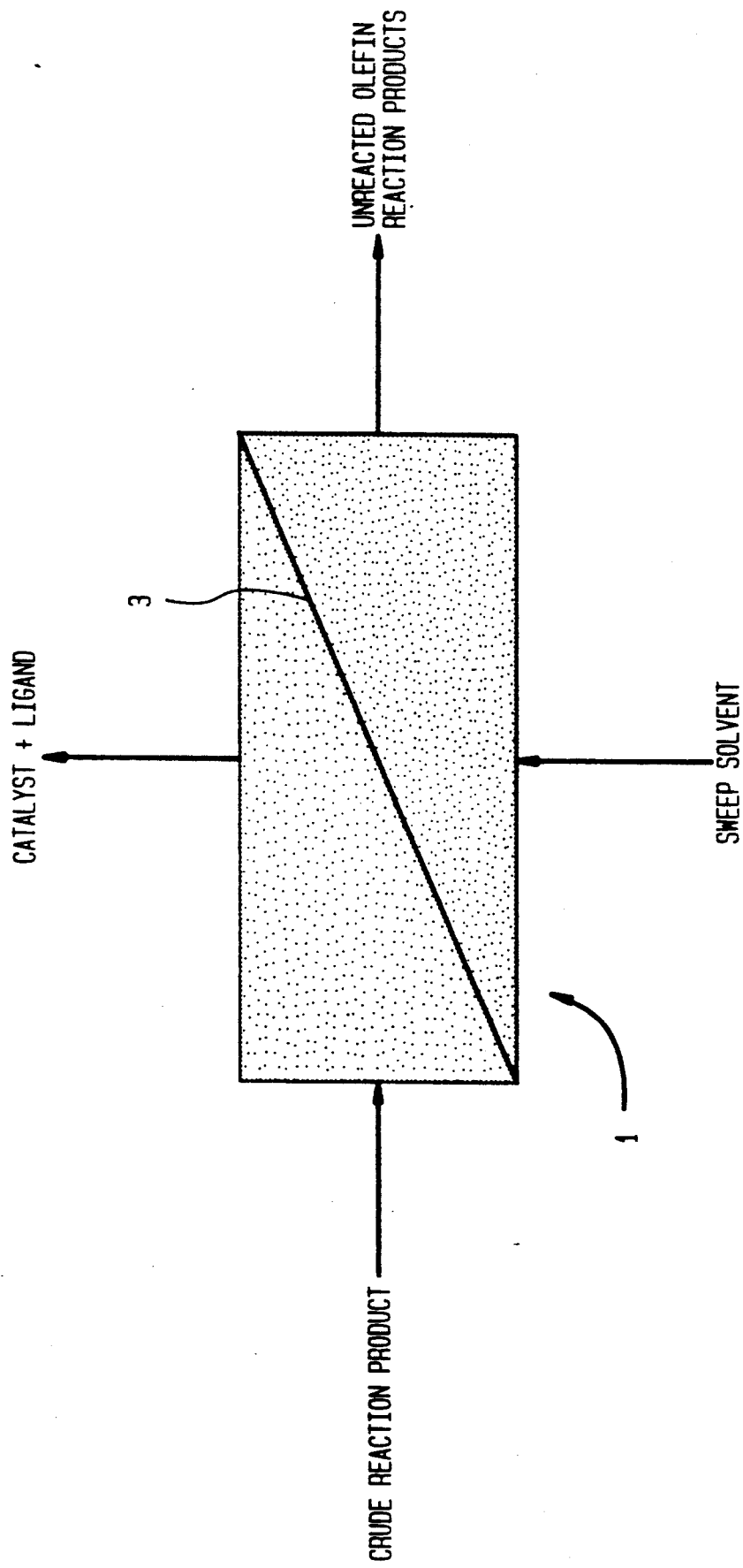
FIG. 1 is a schematic representation of a membrane separator according to the present invention wherein a hydrophobic membrane retains a water soluble Group VIII noble metal-ligand complex catalyst, and permits the passage therethrough of organic hydroformylation reaction product and unreacted olefin feed.

The present invention can best be described by referring to the attached drawings, wherein FIG. 1 is a schematic representation of a membrane separator 1 comprising a hydrophobic membrane 3. Membrane separator 1 is preferably used to separate a water soluble Group VIII noble metal-ligand complex catalyst from a crude reaction product of a noble metal-catalyzed hydroformylation reaction run in aqueous solution, in an aqueous emulsion or as an aqueous suspension. The crude reaction product typically includes an aqueous phase containing a water soluble Group VIII noble metal-ligand complex catalyst, and an organic phase containing unreacted olefin feed and an organic hydroformylation reaction product. Separation occurs by contacting the crude reaction product with hydrophobic membrane 3 which is capable of allowing a substantial portion of the unreacted olefin feed and organic hydroformylation reaction product to pass therethrough while retaining a substantial portion of the water soluble Group VIII noble metal-ligand complex catalyst. The unreacted olefin feed and organic hydroformylation reaction product which pass through hydrophobic membrane 3 as permeate is then removed from membrane separator 1 for further downstream treatment. The retentate which comprises water soluble Group VIII noble metal-ligand complex catalyst and some of the organic phase constituents is recycled to the hydroformylation reactor.

The organic hydroformylation reaction product and unreacted olefin feed are permeated, either by perstraction or pervaporation, through hydrophobic membrane 3 which retains the water-soluble catalyst quantitatively.

The preferred water soluble ligand is one compound selected from the group consisting of: Na-p-(diphenylphosphino)benzoate, Na-m-(diphenylphosphino)benzenesulfonate, and tris(sodium m-sulfophenyl)-phosphine. And the preferred water soluble noble metal catalyst is rhodium. The noble metal-catalyzed hydroformylation reaction according to the present invention preferably involves the reacting of an olefin with hydrogen and carbon monoxide (synthesis gas) in the presence of a water soluble Group VIII noble metal-ligand complex catalyst, at a temperature in the range between about 80° to 125° C. to produce an aldehyde having a normal to iso ratio in the range of between about 0.5:1 to about 80:1. Optionally, a surfactant may be added to the noble metal-catalyzed hydroformylation reaction. The surfactant is preferably one compound selected from the group consisting of cetyltrimethylammonium bromide, sodium laurate, sodium stearate, and linear dodecylbenzene sulfonate.

Hydrophobic membrane 3 is preferably selected from the group consisting of: a high density polyethylene crosslinked membrane, a natural latex rubber membrane, a polyvinylidene difluoride membrane, a polychlorotrifluoroethylene membrane, and a polytetrafluoroethylene membrane.

Figure 2:
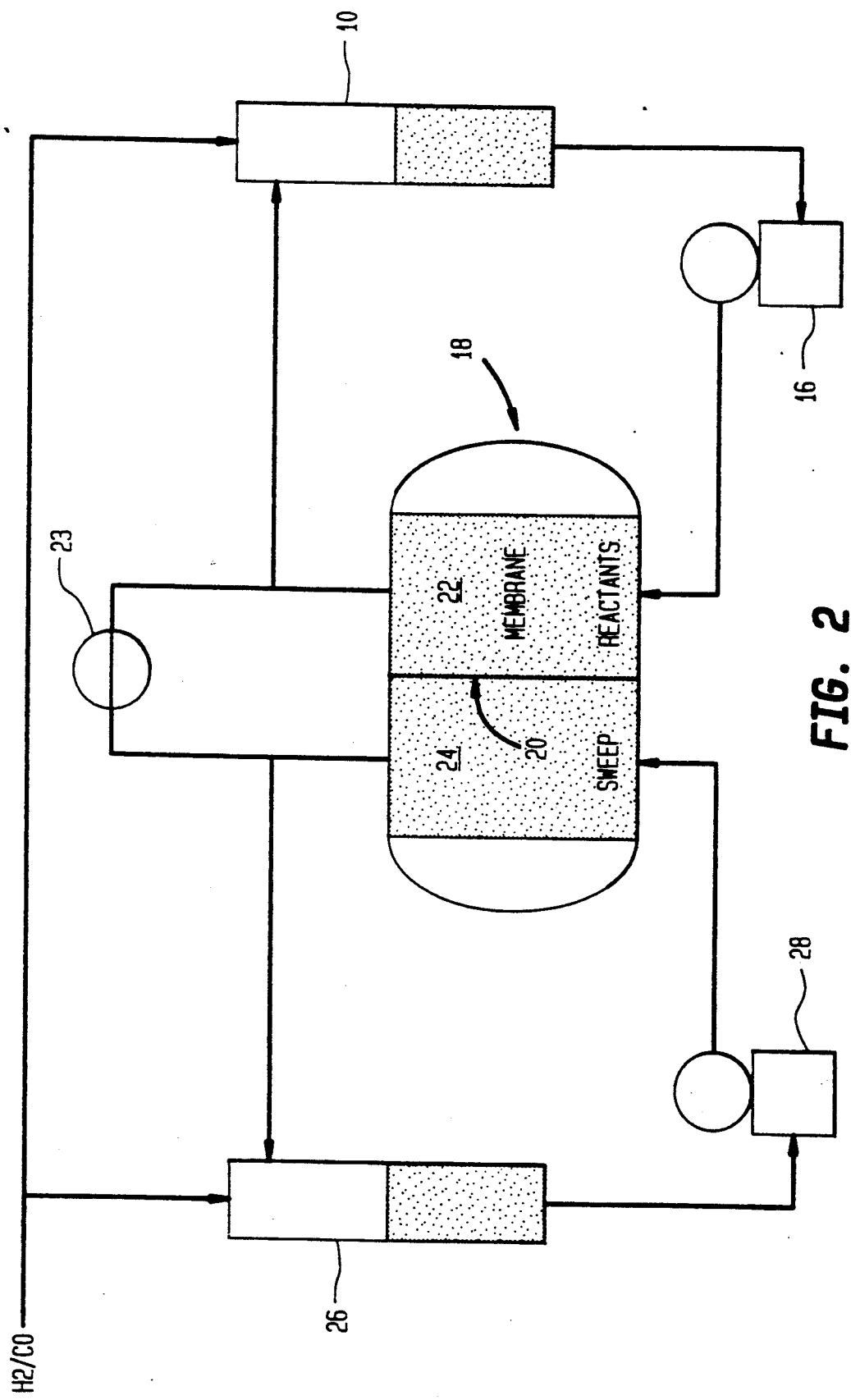
FIG. 2 is a schematic representation of a membrane reactor system according to the present invention which is used to separate water soluble Group VIII noble metal-ligand complex catalysts from organic hydroformylation reaction products and unreacted olefin feed.

The method for producing higher aldehydes and higher alcohols according to the present invention can best be described by referring to FIG. 2, wherein an olefin feedstock is hydroformylated with synthesis gas in the presence of a water soluble Group VIII noble metal-ligand complex catalyst in hydroformylation reactor loop comprising vessel 10, pump 16 and separator 18 to form a crude reaction product. The crude reaction product is typically comprised of an emulsion of the organic phase containing unreacted olefin feed and organic hydroformylation reaction product and an aqueous phase containing a water soluble Group VIII noble metal-ligand complex catalyst. This emulsion of the organic phase and aqueous phase is sent to membrane separator 18 by pumping means 16 for the purpose of removing the water soluble noble metal catalyst from the crude reaction product. Membrane separator 18 includes a hydrophobic membrane 20 which is capable of allowing a substantial portion of the hydroformylation reaction product and unreacted olefin feed to pass from reactant chamber 22 through membrane 20 and into sweep chamber 24, while retaining a substantial portion of the water soluble Group VIII noble metal-ligand complex catalyst within reactant chamber 22. The hydroformylation reaction product and the unreacted olefin feed which pass through membrane 20 are swept away by means of an organic sweep solvent which can be supplied via reactor vessel 26 and pumping means 28.

Hydrophobic membrane 20 is substantially impermeable to water soluble Group VIII noble metal-ligand complex catalyst which are retained as retentate in reactant chamber 22 and thereafter recycled to reaction vessel 10 via pump means 23 for further reaction with the olefinic feedstock. Pump means 23 is also capable of removing the permeate from sweep chamber 24 and thereafter sending the permeate for further downstream treatment.

As shown in FIG. 3, the crude reaction product can optionally be separated into an aqueous layer and a organic layer before it is fed to membrane separator 18. This separation takes place in a settler or other conventional settling tank 30, wherein organic layer 32 rises to the top and aqueous layer 34 settles to the bottom of settler 30. Aqueous layer 34 is recycled to hydroformylation reactor vessel 10 and organic layer 32 is fed to membrane separator 18, wherein water soluble Group VIII noble metal-ligand complex catalyst are retained as retentate and unreacted olefin feed and organic hydroformylation reaction product pass through hydrophobic membrane 20 as permeate. The retentate is recycled to reactor vessel 10 to be again used in the hydroformylation process.

EXAMPLES 1 AND 2

Using an analytical balance, 0.122 grams ($2.74 \times 10^{-4}$ moles) of rhodium acetate dimer containing 0.0551 grams ($5.35 \times 10^{-4}$ g atom) of rhodium was weighed into a 1 dram vial and transferred to the nitrogen dry box for catalyst preparation. Next 1.47 grams ($5.34 \times 10^{-3}$ moles) of diphenylphosphinobenzoic acid and 70 grams of 1N NaHCO$_3$ were weighed into a 125 ml Erlenmeyer flask and heated to approximately 75° C. with magnetic stirring to effect solution of the diphenylphosphinobenzoic acid. The resulting clear and colorless liquid was cooled to room temperature and the rhodium acetate dimer was added. A cloudy orange liquid with orange solids resulted. Finally, 2.0 grams ($5.49 \times 10^{-3}$ moles) of cetyltrimethylammonium bromide (Example 1) was added. A cloudy orange emulsion resulted in fine orange solids. In Example 2, 2.0 grams ($5.49 \times 10^{-3}$ moles) of lauric acid was used in place of the cetyltrimethylammonium bromide.

Into a 500 ml Erlenmeyer flask equipped with a magnetic stirring bar were weighed 179.0 grams (1.28 moles) of decene-1 and 10.6 grams (0.047 mole) of hexadecane. The clear and colorless liquid was deaerated with nitrogen for fifteen minutes with stirring.

The membrane reactor was assembled and the membrane to be tested, 9 cm in diameter, sandwiched by two pieces of Gortex ® (0.2 micron Teflon ®) also 9 cm in diameter, and were mounted in place and the membrane reactor unit was purged with nitrogen. Next the system was evacuated with a vacuum. The catalyst solution was drawn with vacuum to the catalyst side of the membrane and then the decene/hexadecane solution was added to the same side. Finally, the hexene/hexadecane/squalane solution was drawn with vacuum into the sweep side of the unit to act as the perstracting solvent. The hexadecane was employed as an internal standard.

Both the catalyst solution and sweep solution were circulated at a rate of about 1,000 cc/minute. The contents of the membrane reactor unit were pressurized to 100 psi pressure with a 50/50 mixture of hydrogen/carbon monoxide, then heated to about 80° C. in thirty minutes. At 77° C., the hydrogen/carbon monoxide pressure was increased to 150 psi operating pressure and the supply of hydrogen/carbon monoxide kept constant throughout the run.

At the conclusion of the run, the clear and colorless liquid on the sweep side was analyzed for rhodium. The catalyst solution on standing separated into two phases, i.e., clear and colorless upper phase and a yellow-brown lower aqueous phase. The results of the two examples were as follows. Example 1 used a high density polyethylene crosslinked by radiation (1.05 mils) membrane wherein only 0.086 ppm of rhodium were detected in the permeate, i.e., 0.02%. In Example 2 a natural latex rubber membrane demonstrated less than 0.011 ppm rhodium in the permeate, i.e., 0.002%.

EXAMPLE 3

A membrane reactor was assembled with a 9 cm HALAR ® (i.e., a chlorotrifluoroethylene and ethylene copolymer) membrane sandwiched between two pieces of Gortex ® (0.2 micron Teflon ®) also 9 cm in diameter. The HALAR ® membrane was mounted in place and the membrane reactor was purged with nitrogen. Next the system was evacuated with a vacuum. The catalyst solution was drawn with vacuum to the catalyst side of the membrane and then a decene/hexadecane solution was added to the same side. Finally, the hexene/hexadecane/squalane solution was drawn with vacuum into the sweep side of the unit.

Both the catalyst solution and sweep solution were circulated at a rate of about 1,000 cc/minute. The contents of the membrane reactor unit were pressurized to 100 psi pressure with a 50/50 mixture of hydrogen/carbon monoxide then heated to about 80° C. for thirty minutes. At 77° C., the hydrogen/carbon monoxide pressure was increased to 150 psi operating pressure and the supply of hydrogen/carbon monoxide kept constant throughout the run.

At the conclusion of the run, the clear and colorless liquid on the sweep side was analyzed for rhodium. The catalyst solution on standing separated into two phases, i.e., a clear and colorless upper phase and a yellow-brown lower aqueous phase. The HALAR ® membrane permitted only 0.13 ppm of rhodium to permeate therethrough, i.e., less than 0.03%.

It is anticipated that halogenated polymers, as a class, will be advantageous in this type of membrane reactor application. It also appears that hydroformylation reaction products which included a water soluble ligand, such as p-diphenylphosphinobenzoic acid, exhibit satisfactory normal to iso ratios based upon aldehydes, as well as satisfactory turnover number.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A method for separating a water soluble noble metal catalyst from a crude reaction product of a noble metal-catalyzed hydroformylation reaction run in aqueous solution, in an aqueous emulsion or as an aqueous suspension, said crude reaction product including an aqueous phase containing a water soluble Group VIII noble metal-ligand complex catalyst, and an organic phase containing unreacted olefin feed and an organic hydroformylation reaction product, which comprises: (a) contacting said crude reaction product with a hydrophobic membrane capable of allowing a substantial portion of said unreacted olefin feed and organic hydroformylation reaction product to pass therethrough while retaining a substantial portion of said water soluble Group VIII noble metal-ligand complex catalyst, said hydrophobic membrane is selected from the group consisting of: high density polyethylene crosslinked membranes, natural latex rubber membranes, polyvinylidene difluoride membranes, polychlorotrifluoroethylene membranes, and polytetrafluoroethylene membranes; (b) removing unreacted olefin feed and said organic hydroformylation reaction product which passes through said hydrophobic membrane as permeate; and (c) retaining said water soluble Group VIII noble metal-ligand complex catalyst as retentate, wherein said hydrophobic membrane retains at least about 99.5% of said water soluble Group VIII noble metal-ligand complex catalyst.

2. The method according to claim 1 wherein said noble metal-catalyzed hydroformylation reaction includes the steps of: reacting an olefin with hydrogen and carbon monoxide in the presence of a water soluble Group VIII noble metal-ligand complex catalyst, at a temperature in the range between about 80° to 125° C. to produce an aldehyde having a normal to iso ratio in the range of between about 0.5:1 to about 80:1.

3. The method according to claim 2 wherein said ligand is one compound selected from the group consisting of: Na-p-(diphenylphosphino)benzoate, Na-m-(diphenylphosphino)benzenesulfonate, and tris-(sodium m-sulfophenyl)-phosphine.

4. The method according to claim 1 wherein said water soluble Group VIII noble metal catalyst is rhodium.

5. The method according to claim 2 wherein a surfactant is added to said noble metal-catalyzed hydroformylation reaction.

6. The method according to claim 5 wherein said surfactant is one compound selected from the group consisting of: cetyltrimethylammonium bromide, sodium laurate, sodium stearate, and linear dodecylbenzene sulfonate.

7. The method according to claim 1 wherein said organic hydroformylation product and said olefin feed are permeated through said hydrophobic membrane by means of either perstraction or pervaporation.

8. The method according to claim 1 wherein said olefin feed is a $C_4$–$C_{20}$ olefin.

9. The method according to claim 8 wherein said olefin feed is a $C_6$–$C_{16}$ olefin.

10. A method for producing higher aldehydes and higher alcohols which comprises:
(a) hydroformylating an olefinic feedstock with synthesis gas in the presence of water soluble Group VIII noble metal-ligand complex catalyst to form a crude reaction product comprised of an organic phase containing unreacted olefin feed and organic hydroformylation reaction product and an aqueous phase containing a water soluble Group VIII noble metal-ligand complex catalyst;
(b) removing said water soluble Group VIII noble metal-ligand complex catalyst from said crude reaction product by feeding said crude reaction product to a membrane separator which comprises a hydrophobic membrane capable of allowing a substantial portion of said hydroformylation reaction product and unreacted olefin feed to pass therethrough while retaining a substantial portion of said water soluble Group VIII noble metal-ligand complex catalyst, said hydrophobic membrane is selected from the group consisting of: high density polyethylene crosslinked membranes, natural latex rubber membranes, polyvinylidene difluoride membranes, polychlorotrifluoroethylene membranes, and polytetrafluoroethylene membranes;
(c) recovering said hydroformylation reaction product and said unreacted olefin feed as permeate;
(d) retaining said water soluble Group VIII noble metal-ligand complex catalyst as retentate, wherein said hydrophobic membrane retains at least about 99.5% of said water soluble Group VIII noble metal-ligand complex catalyst; and
(e) recycling the retained water soluble Group VIII noble metal-ligand complex catalyst to said hydroformylation step (a).

11. The method according to claim 10 wherein said crude reaction product is separated into an aqueous layer and a organic layer before it is fed to said membrane separator.

12. The method according to claim 11 wherein said organic layer is fed to said membrane separator.

13. The method according to claim 10 wherein said noble metal catalyzed hydroformylation reaction includes the steps of: reacting an olefin with hydrogen and carbon monoxide in the presence of a water soluble Group VIII noble metal-ligand complex catalyst, at a temperature in the range between about 80° to 125° C., to produce an aldehyde having a normal to iso ratio in the range between about 0.5:1 to about 80:1.

14. The method according to claim 13 wherein said water soluble ligand is one compound selected from the group consisting of: Na-p-(diphenylphosphino)benzoate, Na-m-(diphenylphosphino)benzenesulfonate, and tris-(sodium m-sulfophenyl)-phosphine.

15. The method according to claim 14 wherein a surfactant is added to said noble metal catalyzed hydroformylation reaction.

16. The method according to claim 15 wherein said surfactant is one compound selected from the group consisting of: cetyltrimethylammonium bromide, sodium laurate, sodium stearate, and linear dodecylbenzene sulfonate.

17. The method according to claim 10 wherein said water soluble noble metal catalyst is rhodium.

18. The method according to claim 10 wherein said organic hydroformylation product and said olefin feed are permeated through said hydrophobic membrane by means of either perstraction or pervaporation.

19. The method according to claim 10 wherein said olefinic feedstock is a $C_4$–$C_{20}$ olefin.

20. The method according to claim 19 wherein said olefinic feedstock is a $C_6$–$C_{16}$ olefin.

* * * * *